United States Patent
Deguchi et al.

(10) Patent No.: US 10,302,563 B2
(45) Date of Patent: May 28, 2019

(54) APPARATUS AND METHOD OF GAS ANALYSIS USING LASER LIGHT

(71) Applicant: Tokushima University, Tokushima (JP)

(72) Inventors: Yoshihiro Deguchi, Tokushima (JP); Takahiro Kamimoto, Tokushima (JP)

(73) Assignee: Tokushima University, Tokushima (JP)

( * ) Notice: Subject to any disclaimer, the term of this patent is extended or adjusted under 35 U.S.C. 154(b) by 407 days.

(21) Appl. No.: 14/913,296

(22) PCT Filed: Aug. 21, 2014

(86) PCT No.: PCT/JP2014/071877
§ 371 (c)(1),
(2) Date: Feb. 19, 2016

(87) PCT Pub. No.: WO2015/025919
PCT Pub. Date: Feb. 26, 2015

(65) Prior Publication Data
US 2016/0178517 A1 Jun. 23, 2016

(30) Foreign Application Priority Data
Aug. 21, 2013 (JP) .................. 2013-171366

(51) Int. Cl.
*G01N 21/61* (2006.01)
*G01N 21/3504* (2014.01)
(Continued)

(52) U.S. Cl.
CPC .............. *G01N 21/61* (2013.01); *G01J 3/427* (2013.01); *G01J 3/4338* (2013.01);
(Continued)

(58) Field of Classification Search
CPC .. G01N 21/031; G01N 21/3151; G01N 21/39; G01N 2021/399; G01N 21/3504;
(Continued)

(56) References Cited

U.S. PATENT DOCUMENTS 8,928,885 B1 * 1/2015 Luo .................. G01N 21/3504
356/437
2002/0158202 A1 * 10/2002 Webber ................ F23N 5/003
250/339.13
(Continued)

FOREIGN PATENT DOCUMENTS

JP  H11-142327   5/1999
JP  2001-066250  3/2001
(Continued)

OTHER PUBLICATIONS

Kasyutich, V. L., and P. A. Martin. "Towards a two-dimensional concentration and temperature laser absorption tomography sensor system." Applied Physics B 102.1 (2011): 149-162.*
(Continued)

*Primary Examiner* — Harshad R Patel
(74) *Attorney, Agent, or Firm* — Dorsey & Whitney LLP

(57) ABSTRACT

A gas analyzing apparatus includes first and second laser sources that output first and second laser lights, a laser controller that controls the first and second laser sources to vary wavelengths of the first and second laser lights in the respective predetermined wavelength ranges, an optical multiplexer that multiplexes the first and second laser lights to transmit the multiplexed laser light to a target gas, an optical receiver that receives the laser light transmitted through the target gas, and an analyzer that analyzes a temperature and/or a concentration of the target gas based on an electric signal output from the optical receiver. While varying the wavelengths of the laser lights, the laser controller controls amplitudes of the first and second laser lights to differ from each other and varies intensities of the first and second laser lights in the opposite direction.

10 Claims, 12 Drawing Sheets

(51) Int. Cl.
G01J 3/427 (2006.01)
G01N 21/31 (2006.01)
G01N 21/39 (2006.01)
G01J 5/00 (2006.01)
G01J 3/433 (2006.01)
G01J 5/60 (2006.01)
G01K 11/18 (2006.01)
G01K 11/00 (2006.01)

(52) U.S. Cl.
CPC .............. *G01J 5/0014* (2013.01); *G01J 5/601* (2013.01); *G01K 11/00* (2013.01); *G01K 11/18* (2013.01); *G01N 21/3151* (2013.01); *G01N 21/3504* (2013.01); *G01N 21/39* (2013.01); *G01N 2021/399* (2013.01)

(58) Field of Classification Search
CPC ........ G01N 21/61; G01J 3/427; G01J 3/4338; G01J 5/0014; G01J 5/601; G01K 11/00; G01K 11/18
See application file for complete search history.

(56) References Cited

U.S. PATENT DOCUMENTS

| | | | | |
|---|---|---|---|---|
| 2008/0285916 | A1* | 11/2008 | Sappey | G01J 3/1895 385/27 |
| 2009/0303476 | A1* | 12/2009 | Kosterev | G01N 21/1702 356/323 |
| 2009/0323068 | A1 | 12/2009 | Yamakage et al. | |
| 2011/0150035 | A1* | 6/2011 | Hanson | G01K 11/12 374/161 |
| 2012/0188550 | A1 | 7/2012 | Matsuda | |

FOREIGN PATENT DOCUMENTS

| | | |
|---|---|---|
| JP | 2007-199076 | 8/2007 |
| JP | 2008-051598 | 3/2008 |
| JP | 2009-243968 | 10/2009 |
| JP | 2010-169449 | 8/2010 |
| JP | 2011-158426 | 8/2011 |
| JP | 2012-026949 | 2/2012 |
| JP | 2012-137429 | 7/2012 |
| JP | 2012-237684 | 12/2012 |

OTHER PUBLICATIONS

Wood, Michael P., and Krikor B. Ozanyan. "Concentration and temperature tomography at elevated pressures." IEEE Sensors Journal 13.8 (Aug. 2013): 3060-3066.*
Busa, Kristin, et al. "Measurements on NASA langley durable combustor rig by TDLAT: preliminary results." 51st AIAA Aerospace Sciences Meeting including the New Horizons Forum and Aerospace Exposition. Jan. 2013.*
Zhao, Zhenzhen, Fengchun Tian, and Shougiong Liu. "Application and Development Trend of Gas Sensing Technology Based on Absorption Spectroscopy." Green Computing and Communications (GreenCom), 2013 IEEE and Internet of Things (iThings/CPSCom), IEEE International Conference on and IEEE Cyber, Physical and Social Computing. IEEE, Aug. 20-23, 2013.*
"LD Driver with Function and Performance Corresponding to Next Generation Optical Technology." Asahi Data System's ALP-7033CA Product Specification. Aug. 26, 2005. Available online at <http://www.asahi-data.co.jp/4_producets/ALP-7033CAB.html> Accessed online via archive.org on Mar. 12, 2018.*
Deguchi, et al., "Two Dimensional Temperature Measurement using CT Tunable Laser Diode Adsorption Spectroscopy", Journal of the Combustion Society of Japan, vol. 55, No. 173 (2013).
Kiyota, , "2D Concentration measurment of NH3, using CT-tunable diode laser adsorption spectroscopy", CT Handotai Laser Kyusyuho o Mochiita NH3 no Nijigen Nodo Keisoku; Proceedings of Meeting on Automotive Engineers, No. 23-13, May 22, 2013, p. 13-17.
International Search Report received in PCT/JP2014/071877 dated Sep. 22, 2014.
International Preliminary Report on Patentability (Engl. Translation) dated Feb. 25, 2016 received in PCT/JP2014/071877.

* cited by examiner

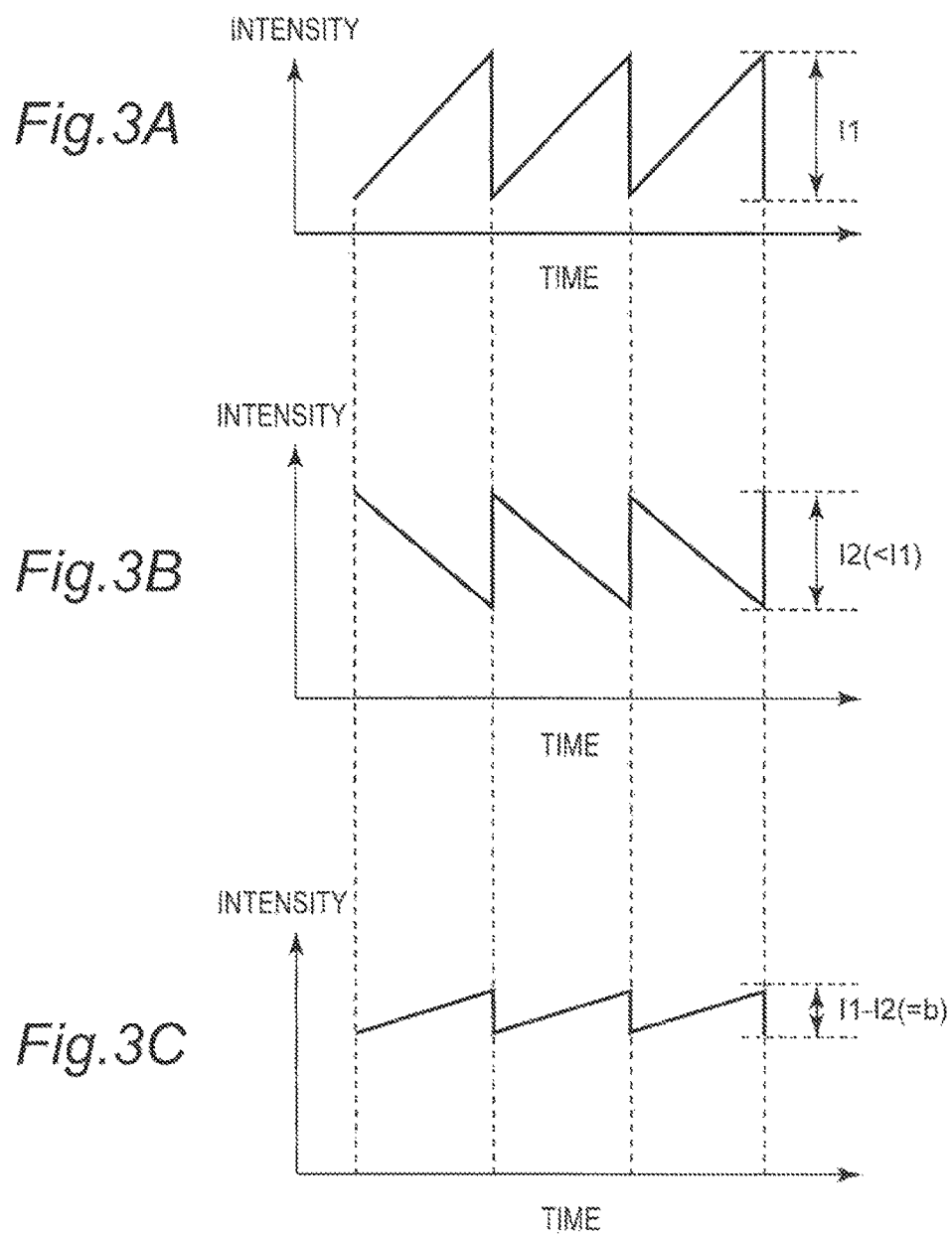
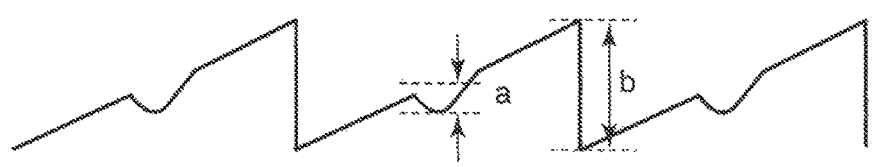

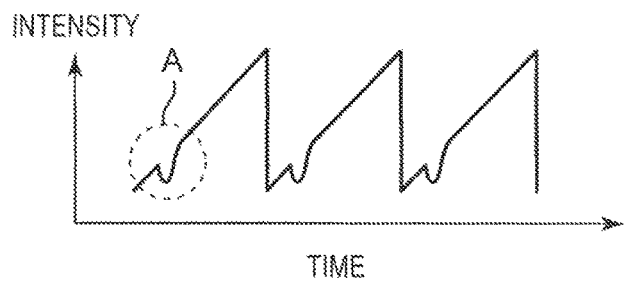
Fig.5A-a
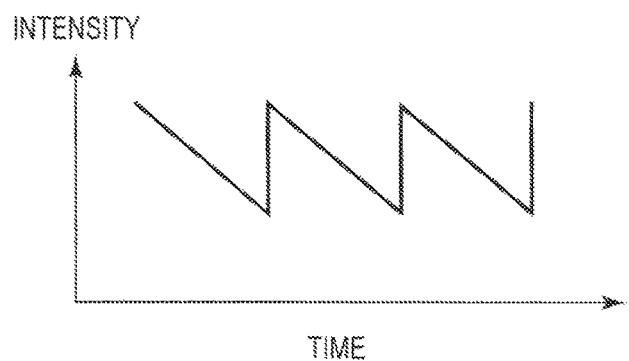
Fig.5A-b
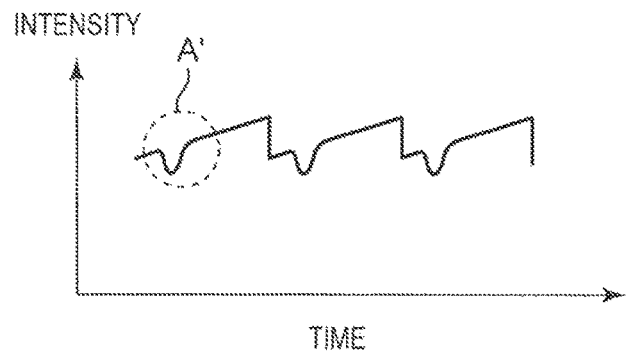
Fig.5A-c

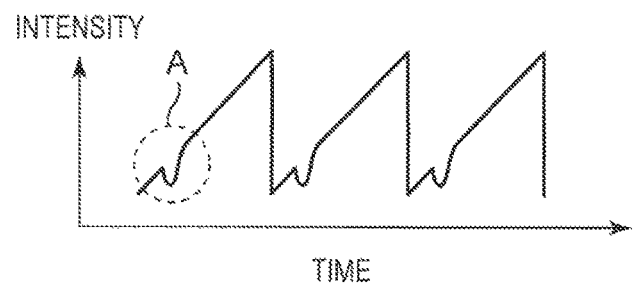
Fig.5B-a
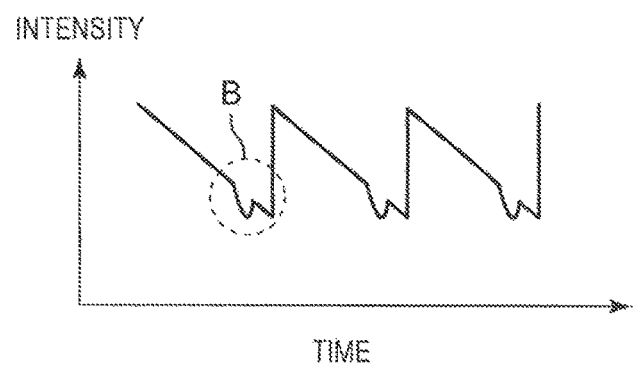
Fig.5B-b
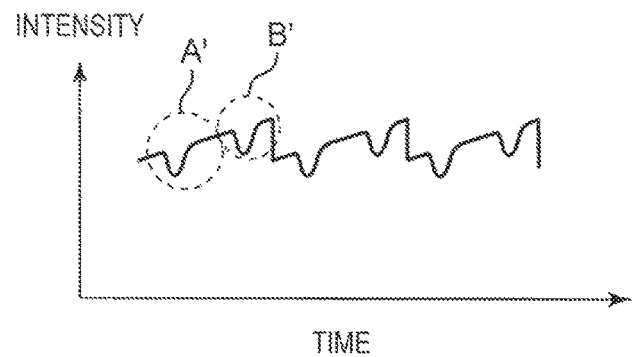
Fig.5B-c (a) 300K, 0.1MPa (b) 800K, 0.1MPa

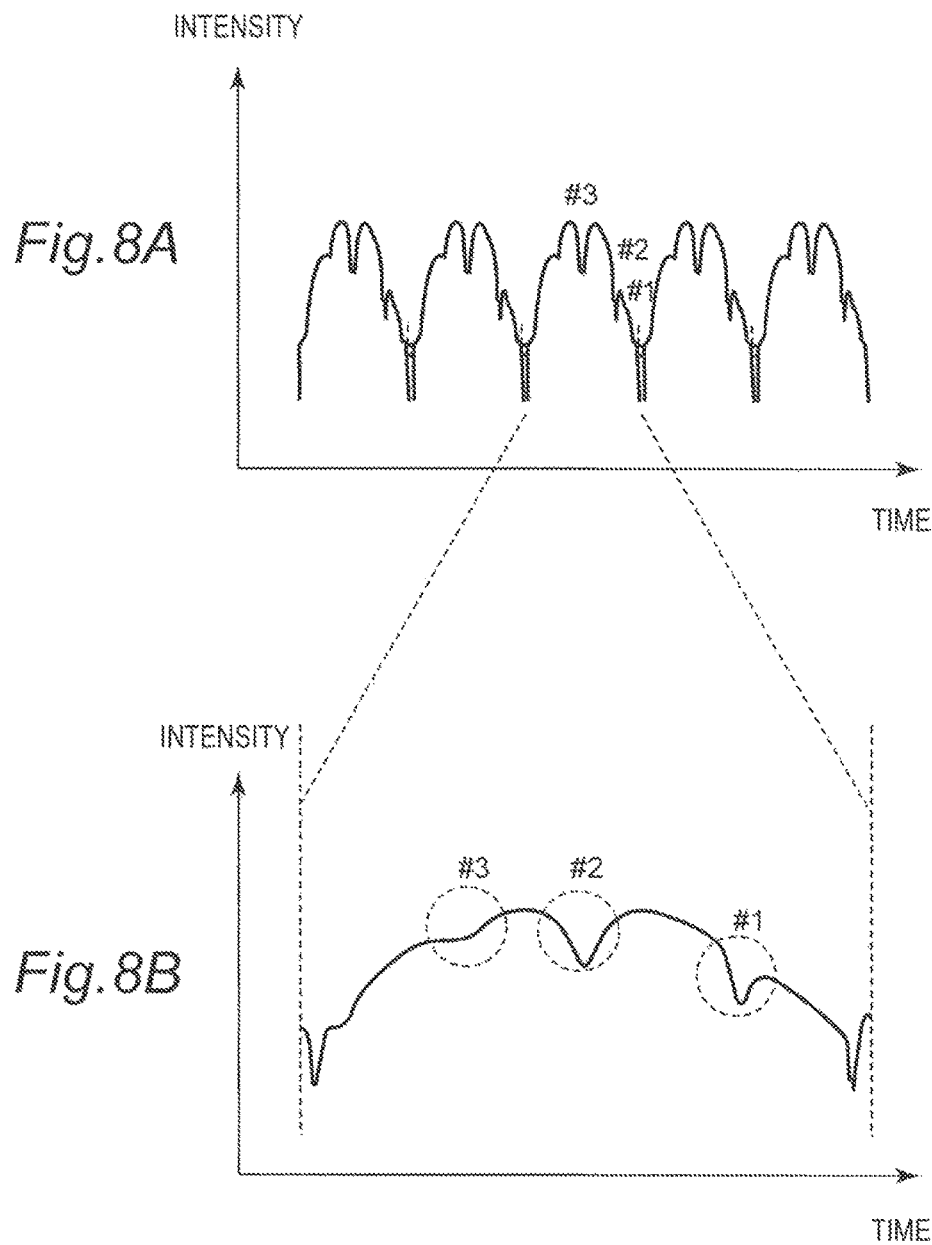

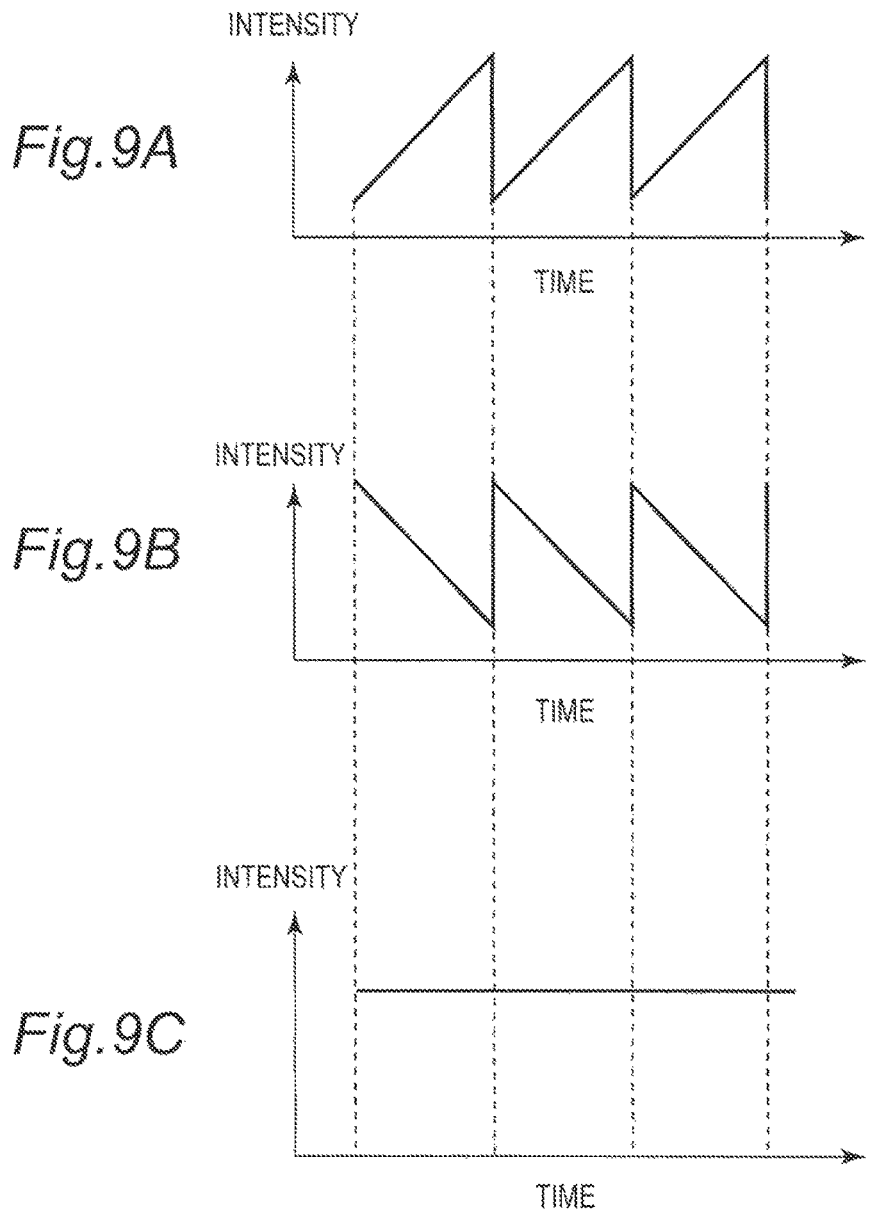

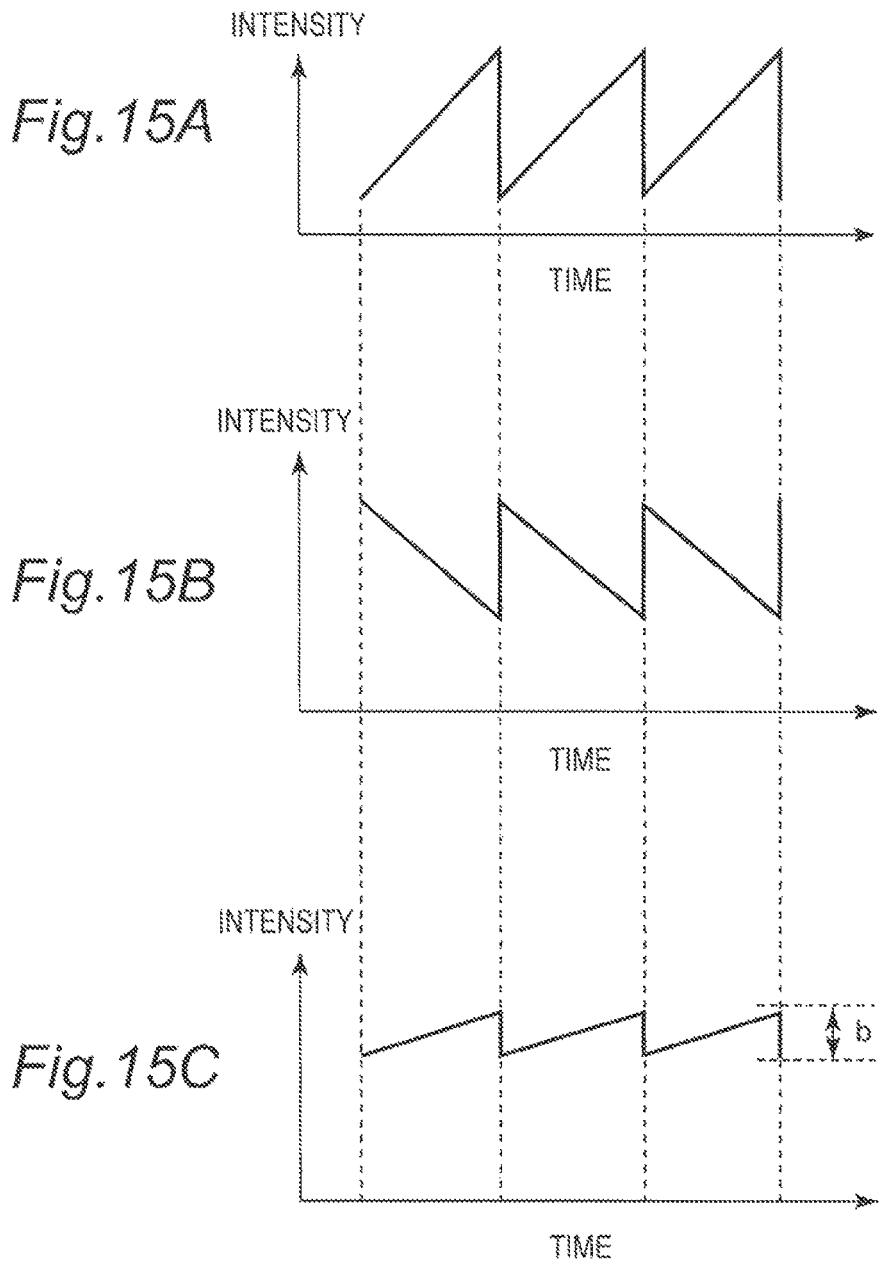

APPARATUS AND METHOD OF GAS ANALYSIS USING LASER LIGHT

RELATED APPLICATIONS

This application is a U.S. National Stage application filing under 35 U.S.C. § 371 claiming priority to International Application No. PCT/JP2014/071877 filed Aug. 21, 2014, which claims priority to Japanese Application No. JP 2013-171366. These applications are incorporated herein by reference, in their entirety, for any purpose.

TECHNICAL FIELD

The present invention relates to an apparatus for detecting a concentration and a temperature of a target gas using a laser light.

BACKGROUND ART

The global environmental conservation and effective use of energy have recently drawn attention in various fields from the viewpoints of global warming, depletion of fossil fuel, and prevention of environmental pollution, and the like. Studies are therefore conducted on various environmental techniques.

It is important for those environmental techniques to clarify in detail combustion structure of combustion phenomenon in each of an engine, a burner, and the like, and transitional behavior thereof. A measurement technique using a semiconductor laser absorption spectroscopy has recently been developed as means of measuring distributions of temperature and concentration in the combustion gas in chronological order and with quick response.

Generally, an absorption spectroscopy is a measuring method utilizing property of gas molecules that absorb an infrared light having a wavelength specific to its chemical species and dependence property of the absorption amount on temperature and concentration of the gas. The concentration and the temperature of the gas to be measured can be measured by determining the ratio ($I_\lambda/I_{\lambda_0}$) of intensity of a transmitted light ($I_\lambda$) to intensity of an incident light ($\lambda_0$) acquired when the incident light is transmitted through an absorbing medium (the gas to be measured) having an even light path length.

One of techniques for detecting the property (concentration and temperature) of the gas to be measured, utilizing the absorption spectroscopy using the semiconductor laser is disclosed in Patent Document 1 and the like.

Patent Document 1 discloses a gas detecting apparatus that couples laser lights from two laser diodes with each other, and applies the coupled laser light to a target gas to calculate the gas concentration based on a measurement light transmitted through the target gas. Specifically, one laser diode generates a laser light having a wavelength to be absorbed by the target gas, and the other laser diode generates a laser light having a wavelength not to be absorbed by the target gas. A modulation signal regulator circuit modulates the laser lights to have substantially the equal amplitude and have the opposite phase, and produces modulated lights La and Lb. An optical multiplexer multiplexes the modulated lights La and Lb with each other to produce a measurement light Ls, and outputs the measurement light Ls to atmosphere of the target gas through an optical fiber and a collimator lens. The measurement light passes through the atmosphere of the target gas and is received by a photoreceiver, and a modulated component of an output signal thereof is extracted by a synchronous demodulating circuit. An arithmetic circuit calculates the concentration of the gas from the extracted modulated component.

In a gas detecting apparatus disclosed in Patent Document 2, a laser diode generating a laser light having a wavelength $\lambda 1$ to be absorbed by a target gas outputs a modulated light La, and the modulated light La enters an optical splitter to be divided therein into two lights including a modulated light La1 and a modulated light La2. A first optical multiplexer receives the one modulated light La1 of the two divided modulated lights, and a modulated light Lb that is output from a laser diode generating a laser light having a wavelength $\lambda 2$ not to be absorbed by the target gas, with the modulated light Lb having an amplitude equal to that of the modulated light La and having a phase opposite to that of the modulated light La. The first optical multiplexer produces a first measurement light Ls1. A second optical multiplexer receives the other modulated light La2 of the two divided modulated lights from the modulated light La, and a modulated light Lc that is output from a laser diode generating a laser light having a wavelength $\lambda 3$ not to be absorbed by the target gas, with the modulated light Lc having an amplitude equal to and a phase opposite to those of the modulated light La. The second optical multiplexer produces a second measurement light Ls2. The first measurement light Ls1 and the second measurement light Ls2 enter a third optical multiplexer to finally produce a measurement light Ls.

When the concentration of the target gas is zero, the component having the wavelength $\lambda 1$ of the measurement light Ls, is not at all attenuated. Therefore the measurement light Ls having cancelled modulated components and a constant intensity enters an optical receiver. When the value of the concentration of the target gas is not zero, the component of the measurement light having the wavelength $\lambda 1$ is attenuated corresponding to the concentration of the gas due to the absorption thereby. Therefore, in the output of the optical receiver, a modulated component appears corresponding to the difference between the component of the measurement light having the wavelength $\lambda 1$ and the components of the light for measurement having the wavelength $\lambda 2$ and the wavelength $\lambda 3$. With the detecting apparatus of Patent Document 1, thereby, the stability of the zero point can be maintained and gas leakage detection can be conducted more precisely regardless of any presence or any absence of various noises such as partial masking during the detection.

Patent Document 3 discloses a method of splitting a laser light with a branching filter into a laser light for measurement and a reference laser light, transmitting the laser light for measurement through a gas, receiving the transmitted light with an optical receiver, and determining an absorption spectrum absorbed by a gas component in the gas from the optical intensity of the received laser light for measurement and the optical intensity of the reference laser light.

Patent Document 4 discloses a method which sets a first time period during which an absorption wavelength specific to a gas-like substance to be measured is modulated with a predetermined frequency, and a second time period during which a wavelength not equal to the specific absorption wavelength is modulated with the predetermined frequency when an oscillation wavelength of a laser light is modulated with a modulation signal at a predetermined frequency. The disclosed method determines an accurate concentration of the gas by subtracting an offset signal measured during the second time period from a gas concentration signal including an offset signal measured during the first time period.

PRIOR ART DOCUMENTS

Patent Documents

Patent Document 1: Japanese Laid-Open Patent Publication No. 11-142327
Patent Document 2: Japanese Laid-Open Patent Publication No. 2001-66250
Patent Document 3: Japanese Laid-Open Patent Publication No. 2008-51598
Patent Document 4: Japanese Laid-Open Patent Publication No. 2011-158426

SUMMARY OF THE INVENTION

Problems to be Solved by the Invention

With the technique disclosed in Patent Document 1, the wavelength of the laser light is fixed and no scanning of the wavelength is conducted. Therefore there is a problem that an influence of noises therefore tends to be received and the measurement sensitivity is degraded.

With the techniques disclosed in Patent Documents 1 to 4, an influence cannot be excluded that is caused by reduction of the intensity of the laser light due to any stain of a window disposed in the optical path and the like. Specifically, when the target gas is measured based on an absorption spectrum, it is important to detect the position (the wavelength) and the magnitude of a portion at which signal intensity is reduced appearing in the absorption spectrum (hereinafter, also referred to as "absorption line"). The laser light transmitted to the target gas would be varied due to factors other than the absorption, such as a stain of a window disposed in the optical path of the laser light, and the like. In such a case, the precision of the gas analysis is degraded because the magnitude of the portion with reduced signal intensity appearing in the absorption spectrum (the absorption line) differs from the magnitude of the portion with reduced signal intensity due to the absorption.

An object of the present invention is to provide a gas analyzing apparatus that enables a high precision analysis on a concentration and a temperature of a gas.

Means for Solving Problems

A gas analyzing apparatus according to the present invention includes: a first laser source that outputs a first laser light; a second laser source that outputs a second laser light; a laser controller that controls the first laser source and the second laser source to vary wavelengths of the first laser light and the second laser light in the respective predetermined wavelength ranges; an optical multiplexer that multiplexes the first laser light and the second laser light with each other to transmit the multiplexed laser light to a target gas to be measured; an optical receiver that receives the laser light transmitted through the target gas to output an electric signal corresponding to an intensity of the received laser light; and an analyzer that analyzes a temperature and/or a concentration of the target gas based on the electric signal output from the optical receiver. While varying the wavelengths of the first laser light and the second laser light, the laser controller controls amplitudes of the first laser light and the second laser light to differ from each other and varies intensities of the first laser light and the second laser light in the opposite direction to each other.

A two-dimensional gas analyzing apparatus according to the present invention includes: a first laser source that outputs a first laser light; a second laser source that outputs a second laser light; a laser controller that controls the first laser source and the second laser source to vary wavelengths of the first laser light and the second laser light in the respective predetermined wavelength ranges; an optical multiplexer that multiplexes the first laser light and the second laser light with each other; a splitter that splits a laser light output from the optical multiplexer into plural laser lights for plural optical paths and transmits the split laser lights to a target gas to be measured through the plural optical paths; plural optical receivers that are disposed corresponding to the respective optical paths, each optical receiver receiving the laser light transmitted through the target gas to output an electric signal corresponding to an intensity of the received laser light; and an analyzer that reconstructs a two-dimensional image concerning distribution(s) of temperature and/or concentration of the target gas based on the electric signals output from the optical receivers. While varying the wavelengths of the first laser light and the second laser light, the laser controller controls amplitudes of the first laser light and the second laser light to differ from each other and varies intensities of the first laser light and the second laser light in the opposite direction to each other.

A gas analysis method according to the present invention includes the steps of: outputting a first laser light and a second laser light while varying wavelengths of the first laser light and the second laser light in the respective predetermined wavelength ranges; multiplexing the first laser light and the second laser light to transmit the multiplexed laser light to a target gas to be measured; receiving the laser light transmitted through the target gas; and analyzing a temperature and/or a concentration of the target gas based on information of the received laser light. When the wavelengths of the first laser light and the second laser light are varied, amplitudes of the first laser light and the second laser light are caused to differ from each other and an intensity of the first laser light and an intensity of the second laser light are varied in the opposite direction to each other.

According to the present invention, the two laser lights are controlled to vary the intensities of the two laser lights in the opposite direction to each other. Thus any variation of the intensity of the laser light transmitted to the target gas can be reduced and the detection precision of the gas analysis can be improved. Especially, by making the amplitudes of the first laser light and the second laser light differ from each other, it is possible to cancel any influence of attenuation due to the effect other than that of the absorption of the intended gas component, so that any degradation of precision of gas analysis can be prevented.

BRIEF DESCRIPTION OF DRAWINGS

FIGS. 3A to 3C are diagrams of temporal variation of light emission intensities during wavelength scanning of the two laser lights to be transmitted to a target gas to be measured in the gas analyzing apparatus of the first embodiment (the case where the amplitudes of the two laser lights are caused to differ from each other).

FIG. 4 is a diagram for explaining correction of an amount of reduction due to absorption, of a received light amount.

FIGS. 5A-a to 5A-c are diagrams for explaining the state where a wavelength component specific to the target gas is absorbed in the laser light transmitted to the target gas.

FIGS. 5B-a to 5B-c are diagrams for explaining the state where a wavelength component specific to the target gas is absorbed in the laser light transmitted to two different target gases.

FIGS. 8A and 8B are each a diagram of a signal waveform that is detected by the optical receiver when two laser lights whose intensities are each varied in a direction reverse to that of each other are transmitted to water vapor.

FIGS. 9A to 9C are diagrams of temporal variation of light emission intensities of two laser lights during wavelength scanning of the two laser lights transmitted to the target gas (when the amplitudes of the two laser lights are equal to each other).

FIGS. 15A to 15C are diagrams for explaining temporal variation of an intensity of a laser light and a voltage applied to an optical receiver in a gas analyzing apparatus of the third embodiment.

MODES FOR CARRYING OUT THE INVENTION

Embodiments of a gas analyzing apparatus according to the present invention will be described with reference to the accompanying drawings.

First Embodiment

1. Configuration of Gas Analyzing Apparatus

Figure 1:
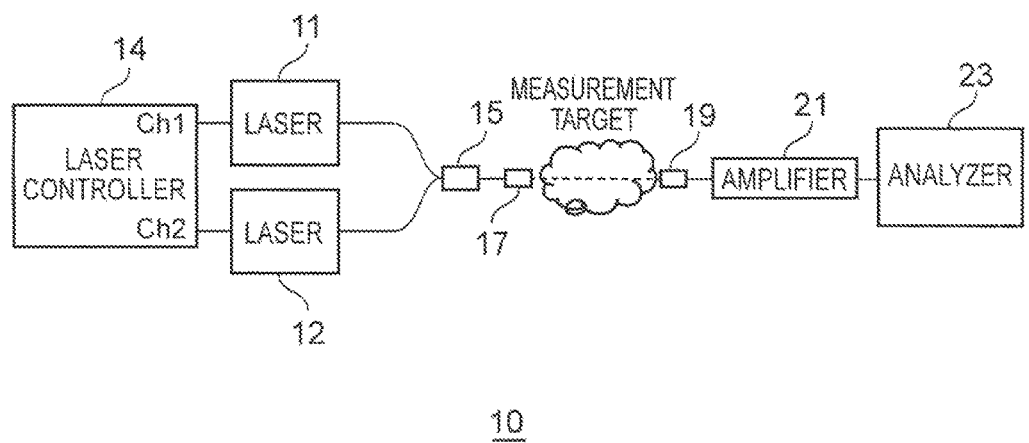
FIG. 1 is a diagram of a configuration of a gas analyzing apparatus in a first embodiment according to the present invention.

FIG. 1 shows a configuration of one embodiment of a gas analyzing apparatus according to the present invention. The gas analyzing apparatus 10 includes two lasers (laser sources) 11 and 12, a laser controller 14, an optical multiplexer 15, and a collimator 17. The gas analyzing apparatus 10 further includes an optical receiver 19, an amplifier 21 that amplifies a signal from the optical receiver 19, and an analyzer 23.

The laser 11 and the laser 12 are each a light source capable of outputting a laser light of a predetermined wavelength band, and, in this embodiment, include a DFB laser. The DFB laser can vary a wavelength of the laser light by varying the value of a current provided to a laser diode (a semiconductor laser). When the wavelength of the laser light is varied, the intensity of the output laser light varies depending on the change in the wavelength. That is, the wavelength of the laser light and the light emission intensity of the laser light have a proportional relation therebetween.

The laser controller 14 controls each of the laser 11 and the laser 12, and thereby controls the wavelength and the intensity of the laser light output from each of the lasers 11 and 12. Specifically, the laser controller controls the laser 11 and the laser 12 to output laser lights by temporally varying (scanning) the wavelengths of the laser lights. For the laser controller 14, any of the various devices available in the market can be used to provide a current to a laser diode to emit light (be driven). For example, an LD driver ALP-7033CC manufactured by Asahi Data Systems Co., Ltd., is usable for the laser controller.

The optical multiplexer 15 multiplexes the two laser lights output from the laser 11 and the laser 12 with each other at branching ratios of 50:50. The collimator 17 collimates the multiplexed light from the optical multiplexer 15 and outputs the collimated light to a target gas to be measured.

The optical receiver 19 receives the laser light transmitted through the target gas and converts the laser light into an electric signal that corresponds to the intensity of the received laser light. The amplifier 21 amplifies the electric signal (an analog signal) from the optical receiver 19 and converts the electric signal into a digital signal.

The analyzer 23 inputs the signal from the amplifier 21, analyzes a waveform (an absorption spectrum) of the input signal to analyze a concentration and a temperature of the target gas. The analyzer 23 can be realized by an information processing device such as, a personal computer.

2. Operation of Gas Analyzing Apparatus

An operation of the gas analyzing apparatus 10 having the above configuration is described below.

The gas analyzing apparatus 10 of the present embodiment transmits a laser light to the target gas while scanning the wavelengths of the laser lights output from the lasers 11 and 12 in the respective predetermined wavelength ranges, analyzes the absorption spectrum of the laser lights acquired therefrom, thereby measuring a concentration and a temperature of the target gas. This operation is described in detail below.

The laser 11 and the laser 12 each output the laser light with intensity of the laser light varied in a direction different from each other under the control of the laser controller 14 (the details of the control of varying the wavelength and the optical intensity of the laser light are described later). The laser lights output from the laser 11 and the laser 12 enter the optical multiplexer 15 to be multiplexed with each other.

The multiplexed light is outputted to a measurement space that contains the target gas (to be measured), through the collimator 17. When the multiplexed light is transmitted through the gas, a laser having a specific wavelength is absorbed by the target gas contained in the gas in the measurement space and the remaining laser light is thereafter received by the optical receiver 19. The received light including information on the absorption of component of the target gas is converted into the electric signal by the optical receiver 19. The amplifier 21 amplifies the electric signal and converts the amplified electric signal into a digital signal which is to be input to the analyzer 23 as a received measurement-light intensity signal.

The analyzer 23 analyzes the concentration and the temperature of the target gas based on the signal waveform of the received measurement-light intensity signal. The analysis is conducted according to the following method, for example. The analyzer 23 stores in advance information on theoretical values of the signal waveform of the measurement reception intensity signal for various concentrations and various temperatures concerning the target gas. The analyzer 23 compares the signal waveform actually acquired by the measurement with the theoretical values of the signal waveform, and identifies the theoretical values of the signal waveform which provides the minimum error between the above two. The concentration and the temperature concerning the identified theoretical values are determined, which are obtained as the measured values of the concentration and the temperature of the target gas.

2.1 Control of Laser Light

The controls are described below for varying the wavelength and the intensity of the laser lights during the scanning of the wavelengths of the laser lights. The control of varying the wavelength and the control of varying the intensity are synchronously conducted for the laser lights output from the lasers 11 and 12.

2.1.1 Variation of Wavelength of Laser Light

Figure 2A:
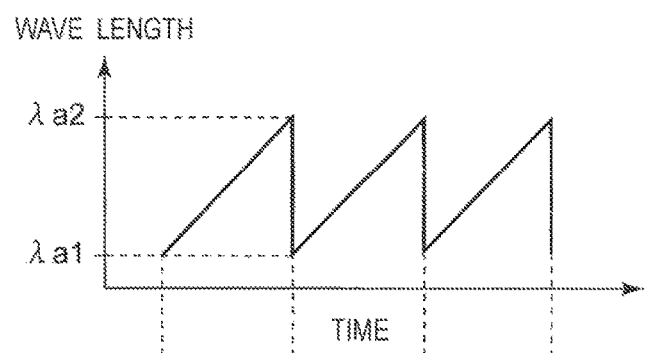
FIGS. 2A and 2B are diagrams of temporal variation of wavelengths in scanning of the wavelengths of two laser lights in the gas analyzing apparatus of the first embodiment.
Figure 2B:
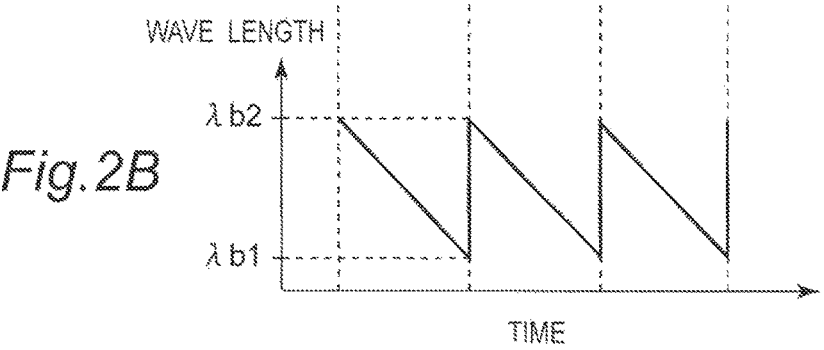

FIGS. 2A and 2B are diagrams for explaining the temporal variation of the wavelengths of the laser lights during the scanning of the laser 11 and the laser 12. FIG. 2A shows the variation of the wavelength of the laser light output from the laser 11. FIG. 2A shows the variation of the wavelength of the laser light output from the laser 12. As shown in FIG. 2, the gas analyzing apparatus 10 periodically varies the respective wavelengths of the laser lights output from the lasers 11 and 12 in the respective predetermined wavelength ranges.

For the laser light output from the laser 11 (hereinafter, referred to as "laser light 1"), the scanning is conducted from a wavelength $\lambda a1$ to a wavelength $\lambda a2$. For the laser light output from the laser 12 (hereinafter, referred to as "laser light 2"), the scanning is conducted from a wavelength $\lambda b1$ to a wavelength $\lambda b2$. The wavelength range for scanning the laser light 1 ($\lambda a1$ to $\lambda a2$) is different from the wavelength range for scanning the laser light 2 ($\lambda b1$ to $\lambda b2$). For example, the wavelength range for scanning the laser light 1 may be set to be a wavelength range including a specific wavelength to be absorbed by the component of the target gas, while the wavelength range for scanning the laser light 2 may be set to be a wavelength range including a specific wavelength not to be absorbed by the component of the target gas. In this case, the component of the target gas can be measured using the absorption line observed in the absorption spectrum of the laser light 1. Alternatively, the wavelength range for scanning the laser light 1 may be set to be a wavelength range including a specific wavelength (a first wavelength) to be absorbed by the component of a first target gas while the wavelength range for scanning the laser light 2 may be set to be a wavelength range including another specific wavelength (a second wavelength) to be absorbed by a component of a gas other than the first target gas (a second target gas). In this case, two gas components can simultaneously be measured using the absorption lines observed in the absorption spectrum of the laser light 1 and the laser light 2 (the details of this are described later with reference to FIG. 5B).

2.1.2 Control of Intensity of Laser Light

In varying the wavelength, the gas analyzing apparatus 10 of the present embodiment controls intensities of the laser lights such that variations of intensities of laser lights of the laser 11 and the laser 12 are opposite to each other. For example, the intensity of the laser light 1 output from the laser 11 is controlled as shown in FIG. 3A and, simultaneously, the intensity of the laser light 2 output from the laser 12 is controlled as shown in FIG. 3B. By multiplexing such two laser lights 1 and 2 of which intensities are reversely changed, the overall variation of the intensities of the laser lights becomes small. The small variation of the intensity of the multiplexed laser light enables shrinkage of a dynamic range of the signal intensity of the laser light (the received optical signal) transmitted through the target gas. Therefore amplification of the overall received optical signal becomes easy, for the purpose of achieving clear observation of the information on feeble absorption lines included in the received optical signal. In FIGS. 3A-3C, the time represented by the axis of abscissa corresponds to the wavelength of the laser light (the same is applied to FIG. 5A and FIG. 5B described later).

Further, in the present embodiment, the amplitudes of the intensities of the laser light 1 and the laser light 2 are made different from each other. In FIGS. 3A and 3B, as an example, the amplitude I1 of the laser light 1 is set to be larger than the amplitude I2 of the laser light 1. Hence the waveform of the multiplexed light of the laser light 1 and the laser light 2 becomes a waveform including a step-like part b (=I1−I2) as shown in FIG. 3C. Using the waveform including such a step-like part b can correct any variation of the amount of the received light in the optical receiver 19 which is caused by other factors than the absorption such as variation of the laser light transmitted to the target gas (such as any stain of a window disposed in the optical path for the laser light). For example, as shown in FIG. 4, when representing a reduction amount due to the absorption actually measured as "a", the size of the step-like part as "b" for the absorption actually measured, and the reduction amount due to the absorption (in the case of no variation of the amount of the received light) as "$a_0$", and the size of the step as "$b_0$" for the absorption, the absorption amount is not influenced by the variation of the received light amount and the influence thereof can be corrected (cancelled) as shown in the following formula.

$$a/b = a_0/b_0$$

FIGS. 5A-a to 5A-c are diagrams for explaining the absorption spectrum acquired when the laser light 1 output from the laser 11 is set to be a laser light in a wavelength range including a specific wavelength to be absorbed by the component of the target gas and the laser light 2 output from the laser 12 is set to be a laser light in a wavelength range including another specific wavelength not to be absorbed by the component of the target gas. When the laser light 1 alone is transmitted to the target gas while varying its intensity as shown in FIG. 3A, an absorption spectrum is acquired that has an intensity reduced portion (an absorption line) A caused by the absorption at a position (a time) that corresponds to the specific wavelength, as shown in FIG. 5A-a. When the laser light 2 alone is transmitted to the target gas while varying its intensity as shown in FIG. 3B, an absorption spectrum is acquired as shown in FIG. 5A-b. When the intensities of the laser light 1 and the laser light 2 are controlled as shown in FIGS. 3A and 3B, respectively and a laser light formed by multiplexing the laser lights 1 and 2 is transmitted to the target gas, an absorption spectrum as shown in FIG. 5A-c is acquired that has an intensity reduced portion (an absorption line) A' caused by the absorption at a position corresponding to the specific wavelength. The condition (the temperature and the concentration) of the target gas can be determined, by determining the magnitude and the position of the intensity reduced portion A' which is caused by the absorption and is observed in the acquired absorption spectrum.

FIGS. 5B-a to 5B-c are diagrams for explaining an absorption spectrum acquired when the laser light 1 output from the laser 11 is set to be a laser light in a wavelength range including a first wavelength to be absorbed by a first target gas component and the laser light 2 output from the laser 12 is set to be a laser light in a wavelength range including a second wavelength to be absorbed by a second target gas. When the laser light 1 alone is transmitted to the target gas while varying its intensity as shown in FIG. 3A, an absorption spectrum is acquired that has an intensity reduced portion (an absorption line) A caused by the absorption at a position (a time) corresponding to the first wavelength as shown in FIG. 5B-a. When the laser light 2 alone is transmitted to another gas while varying its intensity as shown in FIG. 3B, an absorption spectrum is acquired that has an intensity reduced portion (an absorption line) B caused by the absorption at a position (a time) corresponding to the wavelength absorbed by the other gas component as shown in FIG. 5B-b. In this case, especially, the respective wavelength ranges of the laser light 1 and the laser light 2 are set such that the positions at which the intensity reduced portions A and B caused by the absorption by the two gas components appear, that is, the positions of the absorption lines of the two gas components are temporally different from each other. When the intensities of the laser light 1 and the laser light 2 are respectively controlled as shown in FIGS. 3A and 3B and the laser light formed by multiplexing those lights is transmitted to the gas atmosphere that includes the first and the second target gases, an absorption spectrum is acquired that has intensity reduced portions A' and B' caused by the absorption at positions corresponding to the specific wavelengths of the target gases as shown in FIG. 5B-c. As described above, the conditions of the two gas components can be determined by controlling the wavelength ranges (the intensities) of the laser lights 1 and 2 to cause the absorption lines A' and B' to appear at different positions on the time axis.

Next, a signal waveform at the optical receiver 19 is explained, that is acquired when the two laser lights are multiplexed while varying intensities of the two laser lights in opposite direction and the multiplexed lights are transmitted to the target gas.

Figure 6A:
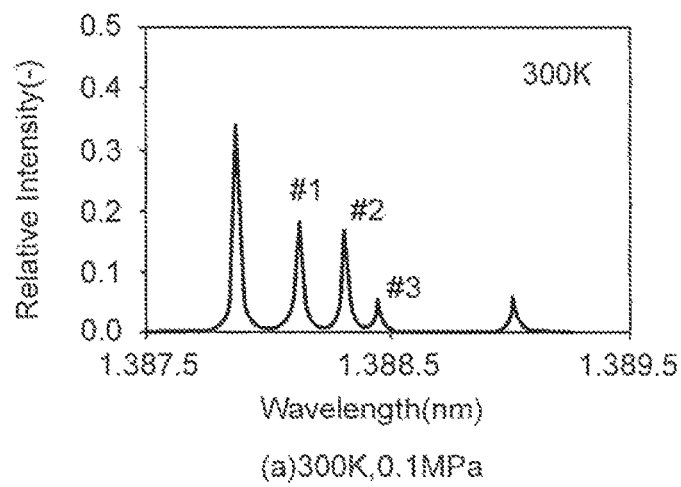
FIGS. 6A and 6B are diagrams for explaining a temperature dependence property of an absorption spectrum of water vapor (FIG. 6A for 300K, FIG. 6B for 800K).
Figure 6B:
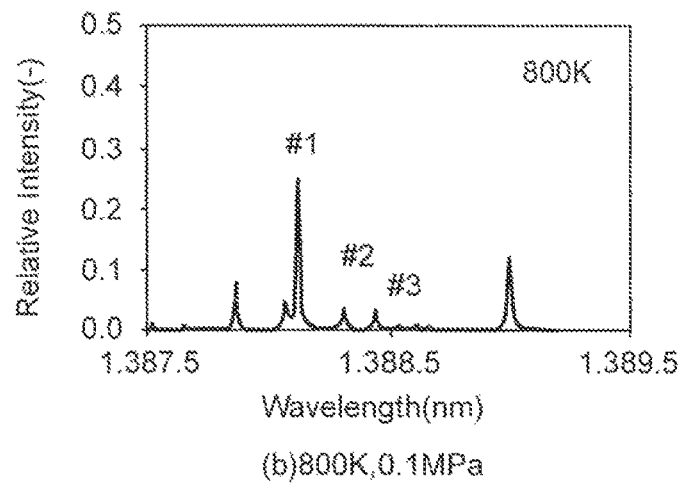

First, temperature dependency of the absorption spectrum of water vapor is described. FIGS. 6A and 6B are diagrams of the temperature dependency of the absorption spectrum of water vapor in a 1388 nm region. An HITRAN database is used for the calculation. FIG. 6A shows an absorption spectrum of water vapor at 300K and FIG. 6B shows an absorption spectrum thereof at 800K. It can be seen from FIGS. 6A and 6B that the intensities of absorption lines #1, #2, and #3 are changed depending on the temperature. It can be seen from these drawings that the absorption spectra of water vapor depend on the temperature. The temperature can be calculated by selecting two absorption lines from the absorption spectrum and calculating the intensity ratio of the absorption lines. The temperature dependency of the absorption spectrum on the concentration has also traditionally been known. Needless to say, not only the temperature of the target gas but also the concentration thereof can also be measured by observing the absorption lines in the absorption spectrum.

Figure 7A:
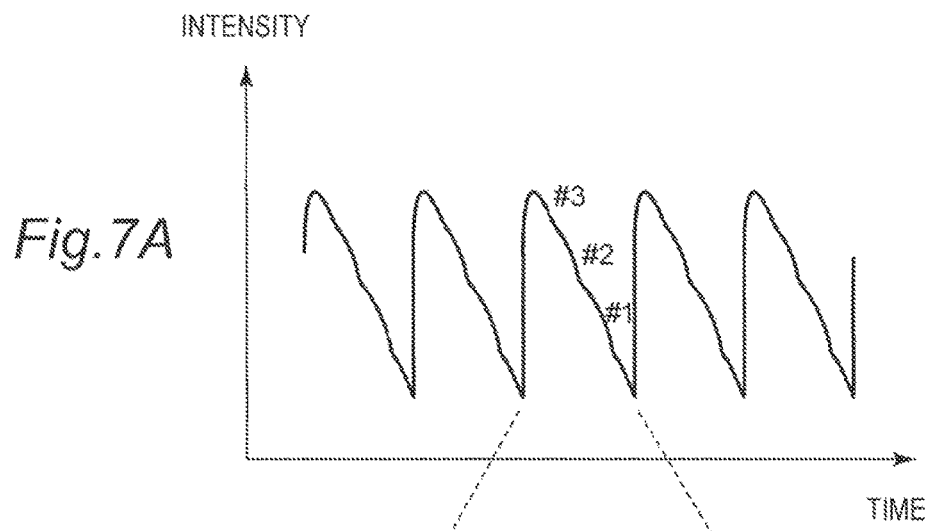
FIGS. 7A and 7B are each diagram of a signal waveform that is detected by an optical receiver when only one laser light is transmitted to water vapor.
Figure 7B:
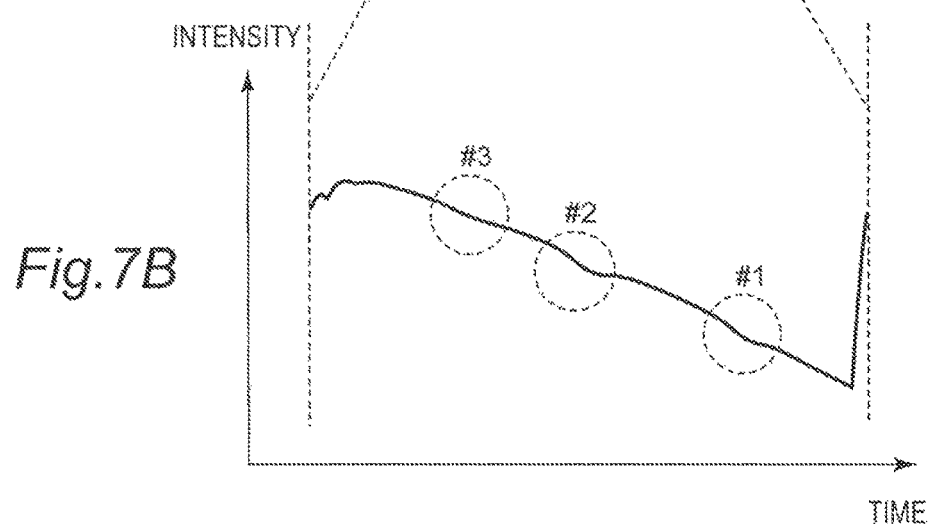

FIGS. 7A and 7B are diagrams of a signal waveform that is detected by the optical receiver when only one laser light is transmitted to water vapor. FIG. 7B is a diagram of a waveform for one cycle shown in FIG. 7A, enlarged in the direction of the time axis. Variations #1, #2, and #3 caused by the absorption can be scarcely read from FIGS. 7A and 7B.

FIGS. 8A and 8B are diagrams of a signal waveform detected by the optical receiver 19 when the two laser lights are multiplexed while varying intensities of the two laser lights in the opposite direction according to the idea of the present embodiment and the multiplexed lights are transmitted to the target gas. FIG. 8B is a diagram of a waveform for one cycle shown in FIG. 8A, enlarged in the direction of the time axis. As shown in FIGS. 8A and 88B, the variations #1, #2, and #3 caused by the absorption more conspicuously appear in the waveform detected using the two laser lights of the present embodiment.

With the method using the one laser light shown in FIGS. 7A and 7B, the absorption amount can be evaluated only to the extent of the level of about $10^{-3}$ relative to the received measurement-light intensity signal. In contrast, when the measurement is conducted using the two laser lights whose intensities are varied in an opposite direction according to the present embodiment as shown in FIGS. 8A and 8B, the received measurement-light intensity signal can be evaluated to the extent of the level of about $10^{-5}$. This level is substantially equal to those of a traditional method of evaluating the secondary differentiation using wavelength modulation and a traditional method of taking a difference from a reference signal.

According to the present embodiment, the laser light formed by multiplexing the two laser lights whose optical intensities are varied in the opposite direction is provided to the target gas to obtain the absorption spectrum. By this manner, the variation of the absorption amount can precisely be detected with a simple configuration by acquiring the absorption spectrum. Further, plural gas components can also be simultaneously measured by using the laser light in the wavelength range including the wavelength absorbed by the gas component different from the target gas component in addition to the laser light in the wavelength range including the wavelength absorbed by the target gas component.

3. Other Configurations (1) In an example shown in FIGS. 3A and 3B, the amplitude I1 (the variation amount) of the laser light 1 emitted from the laser 11 and the amplitude I2 of the laser light 2 emitted from the laser 12 are set to be different value therebetween. However, when the variation of the received amount is small, the amplitudes of the laser light 1 and the laser light 2 may be made equal to each other (see FIGS. 9A-9C). In this case, a multiplexed laser light can be acquired that has small variation of the optical intensity as shown in FIG. 9C.

(2) In the above example, the intensity of the laser light is varied with a saw-tooth shape as shown in FIGS. 3A and 3B. However, the manner of varying the intensity is not limited to this. The laser light 1 and the laser light 2 may also be varied in a sine-wave shape while varying the intensities thereof in the opposite direction. The intensities of the laser light 1 and the laser lights 2 may only be varied so as to reduce the variation of the intensity of the light formed by multiplexing the laser light 1 and the laser light 2. Even when the intensities of the laser lights are varied with the sine-wave shape as such, the same effect can also be achieved as in varying the intensities of the laser lights with the saw-tooth shape, by providing a difference in the amplitude between the laser light 1 and the laser light 2.

(3) In the examples of FIGS. 3A to 3C, FIGS. 5A-a to 5A-c, and FIGS. 5B-a to 5b-c, the intensity of the laser light is varied so that the intensity of the laser light 1 is monotonically increased and the intensity of the laser light 2 is monotonically decreased in one cycle. On the contrary, the intensities of the laser lights may be varied so that the intensity of the laser light 1 is monotonically decreased and the intensity of the laser light 2 is monotonically increased.

(4) Though the wavelength range ($\lambda a1$ to $\lambda a2$) for the scanning of the laser light 1 and the wavelength range ($\lambda b1$ to $\lambda b2$) for the scanning of the laser light 2 are set to be different wavelength ranges in the above examples. However the wavelength ranges for the scanning may partially overlap with each other, when the positions of the absorption lines appearing in the absorption spectra by the laser light 1 and the laser light 2 are different from each other.

(5) In the example of FIGS. 5B-a to 5b-c, it is described that the laser light 1 and the laser light 2 are controlled to cause the absorption lines for the two different target gases to appear at the different positions in the absorption spectra by the laser light 1 and the laser light 2. When the wavelength ranges for the scanning of the laser light 1 and the laser light 2 include the specific wavelength of the same target gas, the laser light 1 and the laser light 2 may be controlled to cause the absorption lines for the same target gas to appear at the different positions in the absorption spectra by the laser light 1 and the laser light 2.

4. Conclusion

As above, the gas analyzing apparatus 10 of the present embodiment includes the laser 11 that outputs the laser light 1, the laser 12 that outputs the laser light 2, the laser controller 14 that controls the lasers 11 and 12 to vary the wavelengths of the laser light 1 and the laser light 2 in the respective predetermined wavelength ranges, the optical multiplexer 15 that multiplexes the laser light 1 and the laser light 2 and transmits the multiplexed laser light to the target gas to be measured, the optical receiver 19 that receives the laser light transmitted through the target gas and outputs the electric signal corresponding to the intensity of the received laser light, and the analyzer 23 that analyzes the temperature and/or the concentration of the target gas based on the electric signal output from the optical receiver 19. While varying the wavelengths of the laser light 1 and the laser light 2, the laser controller 14 controls the amplitudes of the first laser light and the second laser light to differ from each other, and varies the intensity of the laser light 1 and the intensity of the laser light 2 in the opposite direction to each other.

When the wavelengths of the laser light 1 and the laser light 2 are varied, the intensity of the laser light 1 and the intensity of the laser light 2 are varied in the opposite direction. With this control, any variation of the optical intensity can be reduced in the light formed by multiplexing the laser light 1 and the laser light 2, that is provided to the target gas. The evaluation limit of the absorption amount can thereby be expanded. Because any splitters and many optical multiplexers are not necessary to produce the laser lights to be transmitted to the target gas, the structure of the gas analyzing apparatus can be simplified. By making the amplitude of the laser light 1 and the magnitude of the amplitude of the laser light 2 different from each other, any variation can be cancelled, even when the variation occurs in the received light amount at the optical receiver 19 due to factors other than the absorption, such as variation of the laser light provided to the target gas and the like.

The light emission intensity of the first laser light and the light emission intensity of the second laser light may be varied such that the positions at which the absorption lines appear in the absorption spectrum by the laser light 1 and the positions at which the absorption lines appear in the absorption spectrum by the laser light 2 are different from each other. According to this configuration, plural target gas components can simultaneously be measured.

The laser light 1 may be varied in the wavelength range including the specific wavelength absorbed by the component of the target gas and the laser light 2 may be varied in the wavelength range including the specific wavelength not absorbed by the component of the target gas or in the wavelength range including the wavelength absorbed by the component of a gas other than the target gas. The component of the target gas can thereby be measured from the absorption spectrum by the laser light 1.

Second Embodiment

The first embodiment describes the configuration of the gas analyzing apparatus including one path (an optical path) and measuring one-dimensionally the condition of the target gas. The present embodiment describes a configuration of a two-dimensional gas analyzing apparatus that enables the measurement in plural paths for two-dimensional measurement of a concentration and a temperature of the target gas.

Generally known X-ray CT (Computed Tomography) is a technique for configuring a cross-section of an object by scanning the object using an X-ray, dividing the cross-section of the object, measuring an X-ray absorption amount for each of the divided elements, and collecting pieces of information on the X-ray absorption amount of the number equal to an unknown number. In the case where the target gas includes large amounts of components such as water vapor and carbon dioxide, when an emitted light is transmitted through those chemical species each having an absorption spectrum specific thereto, the emitted light is partially absorbed at a wavelength and is thereby attenuated. According to the absorption spectroscopy, the absorption amount is measured as the integral value of the optical paths passing through, the measurement space. A two-dimensional temperature distribution can be measured by transmitting plural laser lights to the measurement space and reconfiguring a two-dimensional image using the CT.

1. Configuration of Two-Dimensional Gas Analyzing Apparatus

Figure 10:
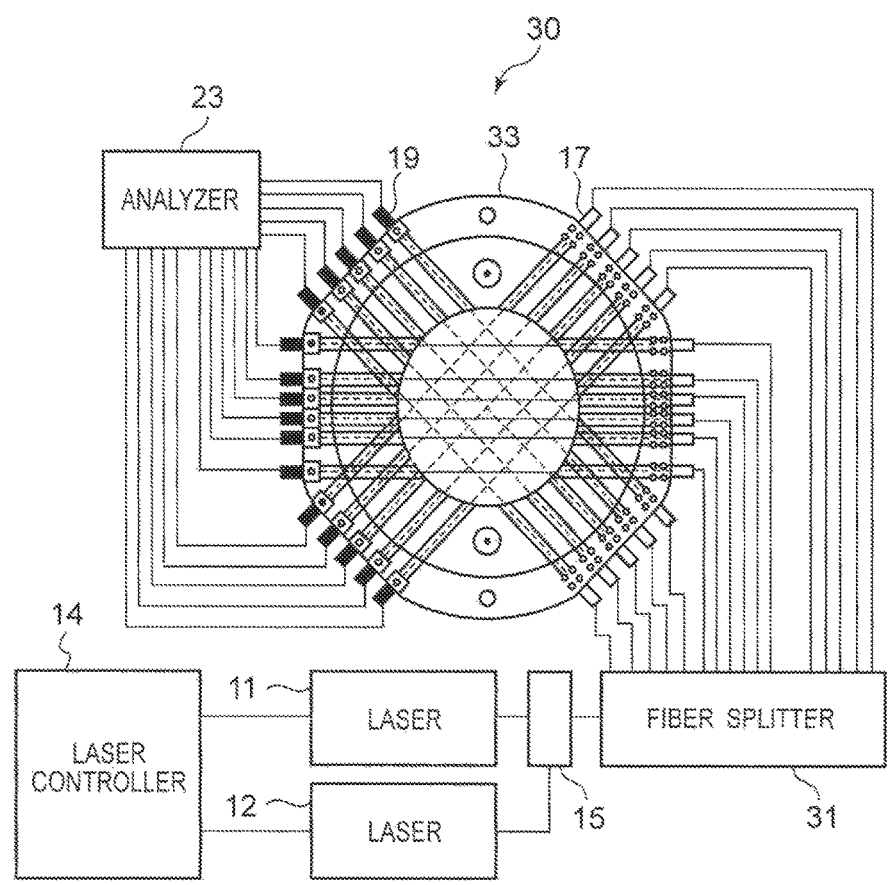
FIG. 10 is a diagram of a configuration of a two-dimensional gas analyzing apparatus in a second embodiment of the present invention.

FIG. 10 shows a configuration of a two-dimensional gas analyzing apparatus capable of two-dimensionally measuring a concentration and a temperature of a target gas to be measured. The two-dimensional gas analyzing apparatus 10a includes two lasers 11 and 12, a laser controller 14, an optical multiplexer 15, a fiber splitter 31, a measurement cell 30, and an analyzer 23.

The measurement cell 30 includes an opening and includes a substantially circular frame 33. To measure intensities of transmitted lights of sixteen optical paths, the frame 33 is attached with sixteen collimators 17 and sixteen optical receivers 19 each disposed facing the corresponding collimator 17.

In the measurement cell 30, a pair of the collimator 17 and the optical receiver 19 forms a path (an optical path) at the opening of the measurement cell 30. The measurement cell 30 includes sixteen paths (the optical paths). Each of the paths (the optical paths) is configured to be included in the same plane and, in this plane, the two-dimensional measurement is enabled. Hereinafter, the normal line direction of the plane including each of the paths (the optical paths) is referred to as "normal line direction of the measurement cell 30".

The amplifier 21 described in the first embodiment is not shown in FIG. 10 because of the convenience for the explanation. In the present embodiment, a device having the same or equivalent function is also provided.

The measurement cell 30 having such a configuration is disposed in the measurement space that contains the target gas and the two-dimensional gas analyzing apparatus 10a conducts measurement for the gas component in the opening of the measurement cell 30.

The laser 11 outputs, for example, a laser light in the wavelength range including a specific wavelength absorbed by a component of the target gas, and the laser 12 outputs a laser light in the wavelength range including a specific wavelength not absorbed by the target gas component or a wavelength absorbed by another gas component. The laser 11 and the laser 12 output laser lights whose intensities are varied in the opposite direction to each other. The laser lights emitted from the laser 11 and the laser 12 enter the optical multiplexer 15 to be multiplexed therein.

The lights emitted from the laser 11 and the laser 12 and multiplexed in the optical multiplexer 15 enter the fiber splitter 31. The fiber splitter 31 splits the multiplexed light to guides the split laser lights into sixteen collimators 17. The split laser lights are outputted to the measurement space through the collimators 17. The laser lights transmitted through the measurement space are received by the optical receivers 19, are converted into electric signals, and are input into the analyzer 23.

The analyzer 23 analyzes the signal waveforms from the optical receivers 19 and reconstructs a two-dimensional image that shows the distribution(s) of the concentration and/or the temperature of the gas component. The reconstruction of the two-dimensional image can be conducted using an existing CT technique.

Although an example where the number of paths (the optical paths) is 16 has been described in the above example, the number of paths (the optical paths) is not limited to 16 and may be 8, 12, or the like.

2. Applications

Some applications of the two-dimensional gas analyzing apparatus 10a of the present embodiment are described below.

(1) Application 1

Figure 11:
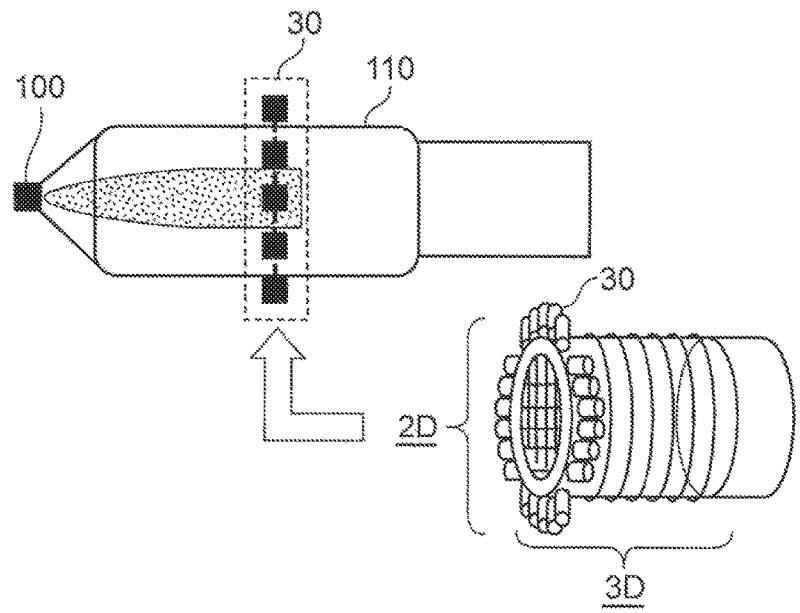
FIG. 11 is a diagram for explaining an application of a two-dimensional analyzing apparatus to a burner.

The two-dimensional gas analyzing apparatus 10a is applicable to detection of a combustion condition (a temperature and a concentration of a target gas to be measured) in a combustion chamber of a burner for a boiler used in a thermal electric power plant and the like. FIG. 11 is a diagram for explaining application of the two-dimensional gas analyzing apparatus 10a of the present embodiment to a burner for a boiler. For example, the measurement cell 30 is disposed at the boiler as shown in FIG. 11 so that the combustion condition in a combustion chamber 110 of a burner 100 can two-dimensionally be measured. Further, the plural measurement cells 30 may be disposed at the combustion chamber 110 side by side in the normal line direction thereof so that the combustion condition can also be three-dimensionally (3D) measured.

(2) Application 2

Figure 12:
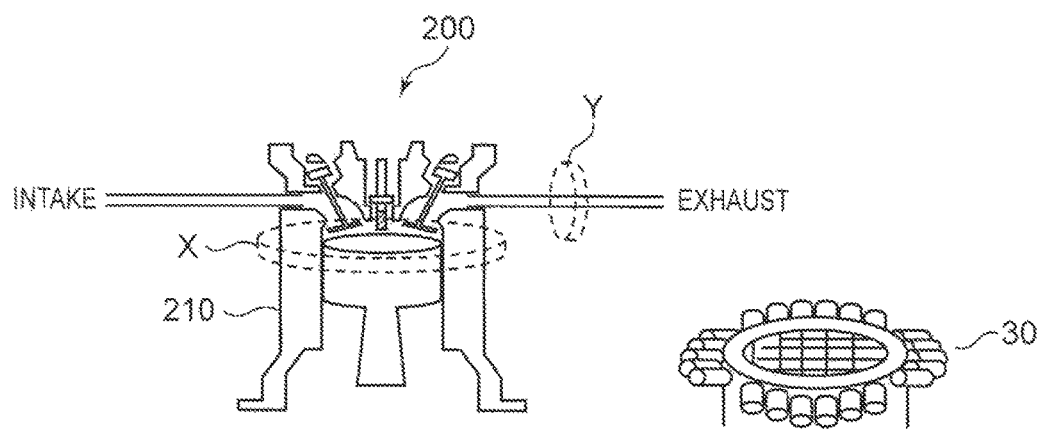
FIG. 12 is a diagram for explaining an application of the two-dimensional analyzing apparatus to an engine.

The two-dimensional gas analyzing apparatus 10a is applicable to detection of a combustion condition (a temperature and a concentration of a target gas) of an engine for a vehicle. FIG. 12 is a diagram for explaining application of the two-dimensional gas analyzing apparatus 10a of the present embodiment to an engine for a vehicle. For example, the measurement cell 30 is disposed at a cylinder 210 of an engine 200 (at a position X) as shown in FIG. 12 so that the combustion condition in the cylinder can be detected. Further, the measurement cell 30 may be disposed in an exhaust pipe (at a position Y) that is a flow path of exhaust gas discharged from the cylinder 210. The temperature and the concentration of the exhaust gas can thereby be detected. Plural measurement cells 30 may be disposed at the cylinder 210 or the exhaust pipe side by side in the normal line direction thereof so that the condition of the gas can also be three-dimensionally measured.

The above configuration enables the detection of the temperature and the concentration of each of various gases in the cylinder or the exhaust system of the engine, and is useful for clarification of the transitional phenomena of combustion and unburned fuel discharge behavior.

(3) Application 3

Figure 13:
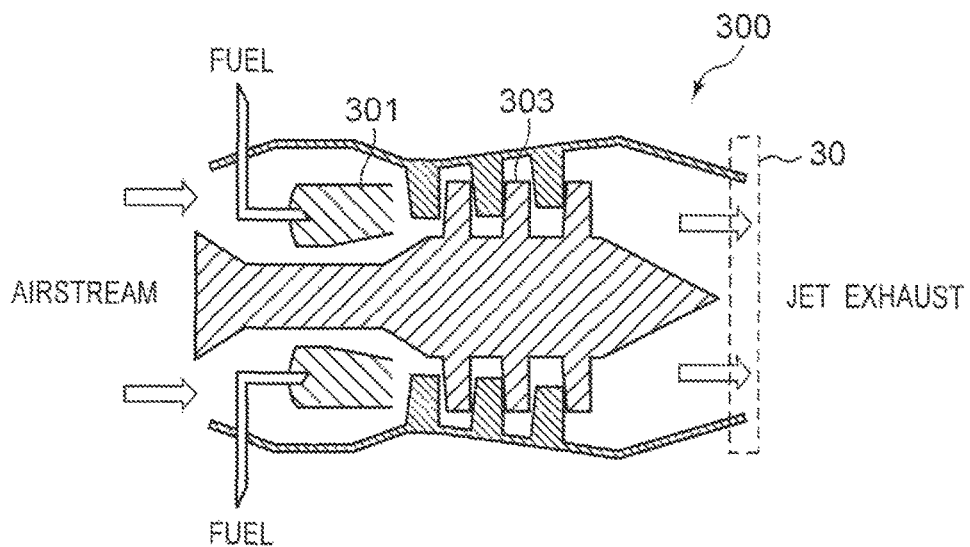
FIG. 13 is a diagram for explaining an application of the two-dimensional analyzing apparatus to a jet engine (an industrial gas turbine).

The two-dimensional gas analyzing apparatus 10a is applicable to detection of a combustion condition (a temperature and a concentration of a target gas) of each of a jet engine and an industrial turbine. FIG. 13 is a diagram for explaining application of the two-dimensional gas analyzing apparatus 10a of the present embodiment to a jet engine. In a jet engine 300 (or a gas turbine), a taken-in airflow is compressed by a compressor using rotation force of a turbine 303 as its driving force, is mixed with fuel in a combustor 301, and is then combusted. The combustion gas generated by the combustion rotates the turbine 303 and is discharged from a jet orifice to the exterior. The measurement cell 30 may be disposed, for example, in the vicinity of the jet orifice of the jet engine 300 as shown in FIG. 13. The combustion condition in the jet fuel cylinder can thereby be detected. This technique is useful for clarification of vibration phenomenon caused by the flow field and the unevenness of the fuel. Plural measurement cells 30 may be disposed in the vicinity of the jet orifice side by side in the direction of the discharge of the combustion gas, so that the combustion condition can thereby be three-dimensionally detected.

As described above, the configuration of the analyzing apparatus combined with the CT technique and the lasers may be applied to the approach of measuring two-dimensionally or three-dimensionally distribution of the temperature and the concentration. With this arrangement, this technique can be developed to applications in combustion apparatuses such as a boiler, an engine, and a gas turbine, while achieving simplification, quantification, and sensitivity improvement of the apparatus.

3. Conclusion

The two-dimensional gas analyzing apparatus 10a of the present embodiment includes the laser 11 that outputs the laser light 1, the laser 12 that outputs the laser light 2, the laser controller 14 that controls the laser 11 and the laser 12 to vary the wavelengths of the laser light 1 and the laser light 2 in the respective predetermined wavelength ranges, the optical multiplexer 15 that multiplexes the laser light 1 and the laser light 2, the fiber splitter 31 that splits the laser light output from the optical multiplexer 15 into plural laser lights for the plural optical paths to transmit the split laser lights through the plural optical paths to the target gas, the plural optical receivers 19 that are provided corresponding to the respective plural optical paths, the plural optical receivers 19 receiving the laser light transmitted through the target gas to output the electric signal corresponding to the intensity of the received laser light, and the analyzer 23 that reconstructs the two-dimensional image concerning the distribution(s) of the temperature and/or the concentration of the target gas based on the electric signals output from the optical receivers 19. When varying the wavelengths of the laser light 1 and the laser light 2, the laser controller 14 varies the intensities of the laser light 1 and the laser light 2 in the opposite direction to each other.

The two-dimensional gas analyzing apparatus 10a of the present embodiment enables the two-dimensional measurement of distributions of the temperature and the concentration of the target gas.

Third Embodiment

Although the measurement is conducted using the two laser lights whose optical intensities are varied in the opposite direction to each other in the first embodiment, a configuration of a gas analyzing apparatus conducting measurement using only one laser light is described in the present embodiment.

Figure 14:
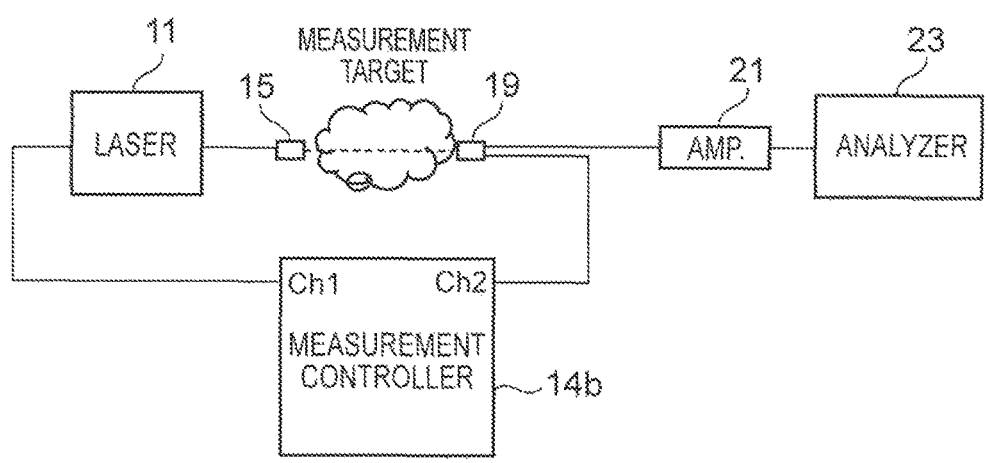
FIG. 14 is a diagram of a configuration of a gas analyzing apparatus in a third embodiment of the present invention.

FIG. 14 shows the configuration of the gas analyzing apparatus of the third embodiment. The gas analyzing apparatus 10b of the third embodiment includes one laser 11, a collimator 17, an optical receiver 19, an amplifier 21, an analyzer 23, and a measurement controller 14b.

The measurement controller 14b controls the intensity of the laser light output from the laser 11 and varies a voltage (a current) to be applied to the optical receiver 19 (a photo-detector) synchronizing with the variation of the intensity. FIGS. 15A and 15B show the variation of the intensity of the laser light output from the laser 11 controlled by the measurement controller 14b, and the variation of the voltage (the current) to be applied to the optical receiver 19 (the photo-detector).

The measurement controller 14b periodically varies the intensity of the laser 11 as shown in FIG. 15A. Synchronizing with the variation of the intensity, the measurement controller 14b varies the voltage (the current) to be applied to the optical receiver 19 (the photo-detector) in a direction opposite to a direction of varying the intensity of the laser light as shown in FIG. 15B. In this case, the amplitude of the voltage to be applied to the optical receiver 19 (the photo-detector) is set such that the signal output from the optical receiver 19 has a step-like part b as shown in FIG. 15B. As a result, the signal output from the optical receiver 19 is set to be a signal with small variation (Note: the signal shown in FIG. 15C is a signal that is not influenced by any absorption). In this manner, any variation of the signal output from the optical receiver 19 can be reduced also by controlling the voltage to be applied to the optical receiver 19 to vary the voltage in a direction opposite to that of varying the intensity of the laser light synchronizing with the variation of the intensity of the one laser light. The same effect can therefore be achieved as that of the first embodiment. Using the waveform including the step-like part b can correct any variation of the received light amount which occurs at the optical receiver 19 due to a factor other than the absorption (such as any stain of a window disposed in the optical path and the like) such as any variation of the laser light transmitted to the target gas.

The invention claimed is:

1. A gas analyzing apparatus comprising:
a first laser source that outputs a first laser light;
a second laser source that outputs a second laser light;
a laser controller that controls currents provided to the first laser source and the second laser source to vary wavelengths of the first laser light and the second laser light in the respective predetermined wavelength ranges;
an optical multiplexer that multiplexes the first laser light and the second laser light with each other to transmit the multiplexed laser light to a target gas to be measured;
an optical receiver that receives the laser light transmitted through the target gas to output an electric signal corresponding to an intensity of the received laser light; and
an analyzer including a processor that analyzes a temperature and/or a concentration of the target gas based on the electric signal output from the optical receiver, wherein
while varying the wavelengths of the first laser light and the second laser light; the laser controller controls a first amplitude of the first laser light and a second amplitude of the second laser light to differ from each other and varies intensities of the first laser light and the second laser light in the opposite direction to each other, and
the analyzer cancels an influence of variation, which is caused by a factor other than the absorption, in the waveform of the electric signal, based on a value of (a/b),
where "a" represents an amount of intensity, reduction due to the absorption detected in a waveform of the electric signal from the optical receiver, and "b" represents a difference between the first amplitude of the first laser light and the second amplitude of the second laser light.

2. The gas analyzing apparatus according to claim 1, wherein
the laser controller varies a light emission intensity of the first laser light and a light emission intensity of the second laser light to cause a position at which an absorption line appears in an absorption spectrum by the first laser light to be different from a position at which an absorption line appears in an absorption spectrum by the second laser light.

3. The gas analyzing apparatus according to claim 1, wherein
the laser controller varies the first laser light in a wavelength range including a specific wavelength absorbed by a component of the target gas, and varies the second laser light in a wavelength range including a specific wavelength not absorbed by the component of the target gas or in a wavelength range including a wavelength absorbed by a component of a gas other than the target gas.

4. A two-dimensional gas analyzing apparatus comprising:
a first laser source that outputs a first laser light;
a second laser source that outputs a second laser light;
a laser controller that controls currents provided to the first laser source and the second laser source to vary wavelengths of the first laser light and the second laser light in the respective predetermined wavelength ranges;
an optical multiplexer that multiplexes the first laser light and the second laser light with each other;
a splitter that splits a laser light output from the optical multiplexer into plural laser lights for plural optical paths and transmits the split laser lights to a target gas to be measured through the plural optical paths;
plural optical receivers that are disposed corresponding to the respective optical paths, each optical receiver receiving the laser light transmitted through the target gas to output an electric signal corresponding to an intensity of the received laser light; and an analyzer including a processor that reconstructs a two-dimensional image concerning distribution(s) of temperature and/or concentration of the target gas based on the electric signals output from the optical receivers, wherein while varying the wavelengths of the first laser light and the second laser light, the laser controller controls a first amplitude of the first laser light and a second amplitude of the second laser light to differ from each other and varies intensities of the first laser light and the second laser light in the opposite direction to each other, and the analyzer cancels an influence of variation, which is caused by a factor other than the absorption, in the waveform of the electric signal, based on a difference in amplitude of the laser light between the first laser light and the second laser light.

5. The two-dimensional gas analyzing apparatus according to claim 4, wherein the laser controller varies a light emission intensity of the first laser light and a light emission intensity of the second laser light to cause a position at which an absorption line appears in an absorption spectrum by the first laser light to be different from a position at which an absorption line appears in an absorption spectrum by the second laser light.

6. The two-dimensional gas analyzing apparatus according to claim 4, wherein the laser controller varies the first laser light in a wavelength range including a specific wavelength absorbed by a component of the target gas, and varies the second laser light in a wavelength range including a specific wavelength not absorbed by the component of the target gas or in a wavelength range including a wavelength absorbed by a component of a gas other than the target gas.

7. The two-dimensional gas analyzing apparatus according to claim 4, wherein the analyzer cancels an influence of variation, which is caused by a factor other than the absorption, in the waveform of the electric signal based on a value of (a/b), where, "a" represents an amount of intensity reduction due to the absorption detected in a waveform of the electric signal from the optical receiver, and "b" represents a difference between the first amplitude of the first laser light and the second amplitude of the second laser light.

8. A gas analysis method comprising:

outputting a first laser light and a second laser light while varying wavelengths of the first laser light and the second laser light in the respective predetermined wavelength ranges;

multiplexing the first laser light and the second laser light to transmit the multiplexed laser light to a target gas to be measured;

receiving the laser light transmitted through the target gas; and analyzing a temperature and/or a concentration of the target gas based on information of the received laser light, wherein when the wavelengths of the first laser light and the second laser light are varied, a first amplitude of the first laser light and a second amplitude of the second laser light are caused to differ from each other and an intensity of the first laser light and an intensity of the second laser light are varied in the opposite direction to each other, and in the analyzing, an influence of variation, which is caused by a factor other than the absorption, in the waveform of the electric signal, is cancelled based on a value of (a/b), where "a" represents an amount of intensity reduction due to the absorption detected in a waveform of the electric signal from the optical receiver; and "b" represents a difference between the first amplitude of the first laser light and the second amplitude of the second laser light.

9. The gas analysis method according to claim 8; wherein when the wavelengths of the first laser light and the second laser light are varied, an intensity of the first laser light and an intensity of the second laser light are varied to cause a position at which an absorption line appears in an absorption spectrum by the first laser light to be different from a position at which an absorption line appears in an absorption spectrum by the second laser light.

10. The gas analysis method according to claim 8, wherein when the wavelengths of the first laser light and the second laser light are varied in the respective predetermined wavelength ranges, the first laser light is varied in a wavelength range including a specific wavelength absorbed by a component of the target gas, and the second laser light is varied in a wavelength range including a specific wavelength not absorbed by the component of the target gas or in a wavelength range including a wavelength absorbed by a component of a gas other than the target gas.

* * * * *